(12) United States Patent
Hong et al.

(10) Patent No.: US 10,327,731 B2
(45) Date of Patent: Jun. 25, 2019

(54) UNIT-OF-MODULE MAPPING PHANTOM FOR MULTIPLE PURPOSES AND MULTIPLE FUSION IMAGES

(71) Applicant: KOREA RESEARCH INSTITUTE OF STANDARDS AND SCIENCE, Daejeon (KR)

(72) Inventors: Cheol Pyo Hong, Gangwon-Do (KR); Bong Young Ahn, Daejeon (KR); Hyo-Min Cho, Daejeon (KR)

(73) Assignee: KOREA RESEARCH INSTITUTE OF STANDARDS AND SCIENCE, Daejeon (KP)

( * ) Notice: Subject to any disclaimer, the term of this patent is extended or adjusted under 35 U.S.C. 154(b) by 35 days.

(21) Appl. No.: 15/541,184

(22) PCT Filed: Dec. 30, 2014

(86) PCT No.: PCT/KR2014/013012
§ 371 (c)(1),
(2) Date: Jun. 30, 2017

(87) PCT Pub. No.: WO2016/108303
PCT Pub. Date: Jul. 7, 2016

(65) Prior Publication Data
US 2017/0347987 A1    Dec. 7, 2017

(51) Int. Cl.
*A61B 6/00*    (2006.01)
*G01R 33/58*    (2006.01)
*A61B 6/03*    (2006.01)
*G09B 23/28*    (2006.01)

(52) U.S. Cl.
CPC .............. *A61B 6/583* (2013.01); *A61B 6/00* (2013.01); *A61B 6/037* (2013.01); *G01R 33/58* (2013.01); *A61B 6/032* (2013.01); *G09B 23/286* (2013.01)

(58) Field of Classification Search
CPC .......... A61B 6/583; A61B 6/037; G01R 33/58
USPC ....................................................... 250/252.1
See application file for complete search history.

(56) References Cited

U.S. PATENT DOCUMENTS

| | | |
|---|---|---|
| 4,719,406 A | 1/1988 | Schaefer et al. |
| 4,816,762 A | 3/1989 | Bohning |
| 6,694,047 B1 * | 2/2004 | Farrokhnia ............ A61B 6/583 |
| | | 378/163 |

(Continued)

FOREIGN PATENT DOCUMENTS

| | | |
|---|---|---|
| KR | 1020040095467 | 11/2004 |
| KR | 1020080006142 | 1/2008 |

(Continued)

*Primary Examiner* — David P Porta
*Assistant Examiner* — Abra S Fein
(74) *Attorney, Agent, or Firm* — Allen, Dyer, Doppelt, + Gilchrist, P.A. Attorneys at Law

(57) ABSTRACT

A medical phantom is an object that models at least a part of the human body by using unit blocks, wherein the unit blocks include: a first unit block having a hexahedral shape of which the inside is empty; and a second unit block. The second unit block has a shape, of which the inside is empty, different from the hexahedral shape The second unit block also has ridges formed at the upper end thereof for stud-and-tube coupling, and has furrows formed at the lower end thereof and enabled to be coupled to the ridges.

12 Claims, 12 Drawing Sheets

(56) References Cited

U.S. PATENT DOCUMENTS

| | | | | |
|---|---|---|---|---|
| 7,818,084 B2* | 10/2010 | Boyden | ................ | A61F 2/06 |
| | | | | 623/1.1 |
| 2012/0292534 A1* | 11/2012 | Geneser | ............ | A61N 5/1069 |
| | | | | 250/492.3 |
| 2012/0330131 A1* | 12/2012 | Nalcioglu | ......... | G01R 33/481 |
| | | | | 600/411 |
| 2015/0173847 A1* | 6/2015 | Hayashi | ............. | A61B 6/032 |
| | | | | 600/431 |
| 2016/0278734 A1* | 9/2016 | Hong | ................ | A61B 6/583 |

FOREIGN PATENT DOCUMENTS

| KR | 20120005185 | 1/2012 |
|---|---|---|
| KR | 20120105185 | 9/2012 |
| KR | 1020130080245 | 7/2013 |

* cited by examiner (a)  (b)

(c)  (d)

(a)

(b)

UNIT-OF-MODULE MAPPING PHANTOM FOR MULTIPLE PURPOSES AND MULTIPLE FUSION IMAGES

TECHNICAL FIELD

The present invention relates to a unit-of-module mapping phantom for multiple purposes and multiple fusion images. Particularly, the present invention relates to manufacturing a unit-of-module mapping block constituting a phantom and a unit-of-module mapping block having a shape and a structure in which a medium required for imaging may be filled in the unit-of-module mapping block, image quality evaluation, human organs and tissues may be simulated, and dosimetry and interventional operation training are available.

BACKGROUND ART

A medical phantom as a model simulating physical properties of the entirety or a part of a human body is used for various types and various purposes in performance evaluation of diagnostic and therapeutic instruments, medical image quality evaluation, dosimetry, interventional operation training and evaluation, and the like. The phantom is able to derive a more consistent result for medical image quality evaluation and optimization than an actual live human body with a subjective physical quantity, thereby enabling accurate diagnosis and treatment. In recent years, with technological development of medical imaging diagnosis and treatment devices, a variety of phantoms corresponding to the technological development has been developed.

However, various and complex phantoms increase the uncertainty of measurement to limit consistency and standardization of the image quality evaluation, fusion accuracy of a fusion medical device, disease related anatomy, and evaluation of pathological information. In addition, since a boundary expression phantom (dummy, and the like), which is a simulated phantom of a whole human body shape, needs to be manufactured in a similar size to the human body, the boundary expression phantom is heavy, expensive and since only a specific size and a specific shape are enabled to be evaluated, there are many difficulties even in operating the boundary expression phantom. Therefore, a phantom with integrated diversity for consistency and standardization is needed.

In manufacturing the phantom for the integrated diversity, unit-of-module manufacturing is a very efficient approach method and such a unit-of-module type is well expressed in tree-shaped unit blocks and LEGO blocks which are infant toys in the related art.

Even in the related art, a brick, which is a unit module of LEGO, is combined to be configured with a certain type of phantom and may be then used to evaluate the performance of an imaging diagnostic apparatus.

However, in the case of the phantom using the LEGO block, since the inside of the block is an empty space, there is a disadvantage that the block needs to be assembled and then, imaged in a certain size container.

That is, although it is possible to assemble the blocks in various forms using blocks, there is a disadvantage in that it is necessary to put a block in a vessel including a signal source in order to generate the signal source required for imaging.

Furthermore, there is also a problem in that a medium having a specific physical property is required inside the block even for the image evaluation and dosimetry.

As a result, in the case of the phantom using the LEGO block, the degree of freedom of the block is limited depending on the size and shape of the container, and the same problem as the phantom widely used in the related art is obtained.

Further, the most important disadvantage of the LEGO block is that the LEGO block is not manufactured for the medical phantom, so there are many limitations in using size, shape, and function for medical use.

In addition, since the Lego shape has a ridge and a furrow in the block, when the Leg shape is simply combined and imaged, the Lego block has a complicated shape, which is very disadvantageous to medical utilization of the image.

Particularly, when the LEGOs having a small physical size are combined, the complexity of the LEGOs becomes very large, and when the physical size is relatively large, there is a disadvantage in that it is disadvantageous in detailed simulation of the human body characteristics. Accordingly, a solution method thereof is required.

DISCLOSURE

Technical Problem

The present invention is contrived to solve the problem in the related art and an object of the present invention is to provide a unit-of-module mapping phantom for multiple purposes and multiple fusion images and a control method thereof to a user.

In detail, the present invention has been made in an effort to provide contents regarding manufacturing of a unit block constituting a phantom and a unit-of-module mapping block having a shape and a structure in which a medium required for imaging may be filled in the unit block, image quality evaluation, and dosimetry and interventional operation training are available.

Meanwhile, the technical objects of the present invention are not limited to the aforementioned technical objects, and other technical objects, which are not mentioned above, will be apparently appreciated by a person having ordinary skill in the art from the following description.

Technical Solution

In order to implement the object, in a medical phantom which models at least a part of a human body by using a plurality of unit blocks, the plurality of unit blocks include: a first unit block having a hexahedral shape of which the inside is empty; and a second unit block having a shape, of which the inside is empty, different from the hexahedral shape, having a plurality of ridges formed at the upper end thereof for stud-and-tube coupling, and having a plurality of furrows formed at the lower end thereof and enabled to be coupled to the plurality of ridges and the medical phantom is determined according to a combination form of the first unit block and the second unit block, at least one hole may be formed on the lateral surfaces of the first unit block and the second unit block and a medium may be injected through the at least one hole.

Further, the second unit block may include a 2-$1^{st}$ block which is a half in a vertical size larger than the first unit block, a 2-$2^{nd}$ block which is twice in vertical size larger than the first unit block, and a 2-$3^{rd}$ block which is a square of the vertical size of the first unit block.

In addition, the second unit block may include, based on a predetermined disk shape, a 2-4th block which is twice in horizontal and vertical sizes larger than the disk shape, a 2-5th block which is ¼ in horizontal and vertical sizes larger than the disk shape, and a 2-6th block which is twice in horizontal and vertical sizes larger than the disk shape.

Moreover, the plurality of ridges may be in a cylindrical shape which protrudes at the upper end of the second unit block and the plurality of furrows may be formed at the lower end of the second unit block in a recessed cylindrical shape to be coupled with the plurality of ridges.

In addition, the first unit block and the second unit block may be made of polycarbonate which is a semi-transparent material.

Further, a plurality of media injected through the at least one hole may have different colors and the media injected through the at least one hole may be distinguished by using a semi-transparent property of the polycarbonate and a characteristic in which the colors of the media are different from each other.

In addition, the media injected through the first hole may include CuSO4, MnCl2, and NiCl2 which are signal sources required for magnetic resonance imaging and Gd-based media, iron oxide-based media, and gel-type media which are capable of exhibiting a contrast effect.

Moreover, the media injected through the first hole may include water, iodine, barium, CaCO3, paraffin, and adipose capable of image evaluation in X-ray computed tomography.

In addition, the media injected through the first hole may include positron-emitting isotopes and gamma-emitting isotopes which are the signal sources of PET and SPECT which are nuclear medical imaging devices.

Further, at least some of the media and air in the first and second unit blocks are discharged to the outside through the at least one hole.

In addition, the medical phantom determined according to a coupling shape of the first and second unit blocks may be used for multiple purposes and may be connected with multiple imaging devices to support multiple imaging.

Moreover, the medical phantom may further include image quality evaluation modules provided in the first and second unit blocks and the medical phantom may evaluate at least some of spatial resolution, contrast resolution, signal-to-noise ratio, uniformity, location and accuracy of cross-section selection, and geometric accuracy using the image quality evaluation module.

Meanwhile, an image diagnostic apparatus related with another embodiment of the present invention for implementing the above-described object may be manufactured by using the above-described medical phantom.

Advantageous Effects

The present invention may provide a unit block for multiple purposes and multiple images, a multi-module medical phantom using the unit block, and a control method to a user.

In detail, the present invention may provide contents regarding manufacturing of a unit block constituting a phantom and a unit-of-module mapping block having a shape and a structure in which a medium required for imaging may be filled in the unit block, image quality evaluation, and dosimetry and interventional operation training are available.

Unlike a single image and a single purpose phantom which is heavy and difficult to operate in the related art, a block-based phantom according to the present invention can be combined in various forms according to a combination of blocks, and can be used for multiple images and multiple purposes and in particular, the unit block is very easy to mass-produce and can be used in various video devices, and as a result, and it is very economical.

Meanwhile, effects which can be obtained in the present invention are not limited to the aforementioned effects and other unmentioned effects will be clearly understood by those skilled in the art from the following description.

DESCRIPTION OF DRAWINGS

The following drawings included in the present disclosure indicate the preferred exemplary embodiments of the present disclosure, and above and other aspects, features and other advantages of the present disclosure will be more clearly understood from the following detailed description taken in conjunction with the accompanying drawings. However, the present disclosure is not limited by the issues only illustrated in the drawings.

BEST MODE

Hereinafter, preferable exemplary embodiments of the present invention will be described with reference to the accompanying drawings. Further, exemplary embodiments described below do not limit the contents of the present invention described in claims and the entire configuration described in the exemplary embodiment cannot be necessary as the technical solution of the present invention.

A phantom means a model which is used as a substitute for research on biological systems such as electromagnetic wave distribution in the human body and search and analysis of specific absorption rate (SAR) of the human tissue.

In this case, quantitative evaluation of the electromagnetic wave received by the human body is performed by the SAR, and actually, since it is difficult to measure the quantitative evaluation, so-called phantom that is the same as human body is created, and the quantitative evaluation is estimated by measurement of an electric field and temperature rise in the phantom, animal experiments, and analysis of the electromagnetic field when the electromagnetic wave is irradiated.

The phantom has an external shape having a similar size to a human tissue structure and it is necessary to have a specific dielectric constant ε, a conductivity σ, and a density ρ of the human tissue at each measurement frequency.

Representatively, the phantom may be used as a model used instead of the human body to determine a radiation dose received to the human body and may mean an object which is used for simulating and measuring attenuation and scattering of radiation or distribution of a radioactive material in the object.

Meanwhile, a medical phantom is a model that simulates physical properties of the whole or a part of the human body and used in various shapes and various purposes in diagnosis and performance evaluation of treatment devices, evaluation of medical image quality, dosimetry, interventional operation training and evaluation, and the like.

Figure 1:
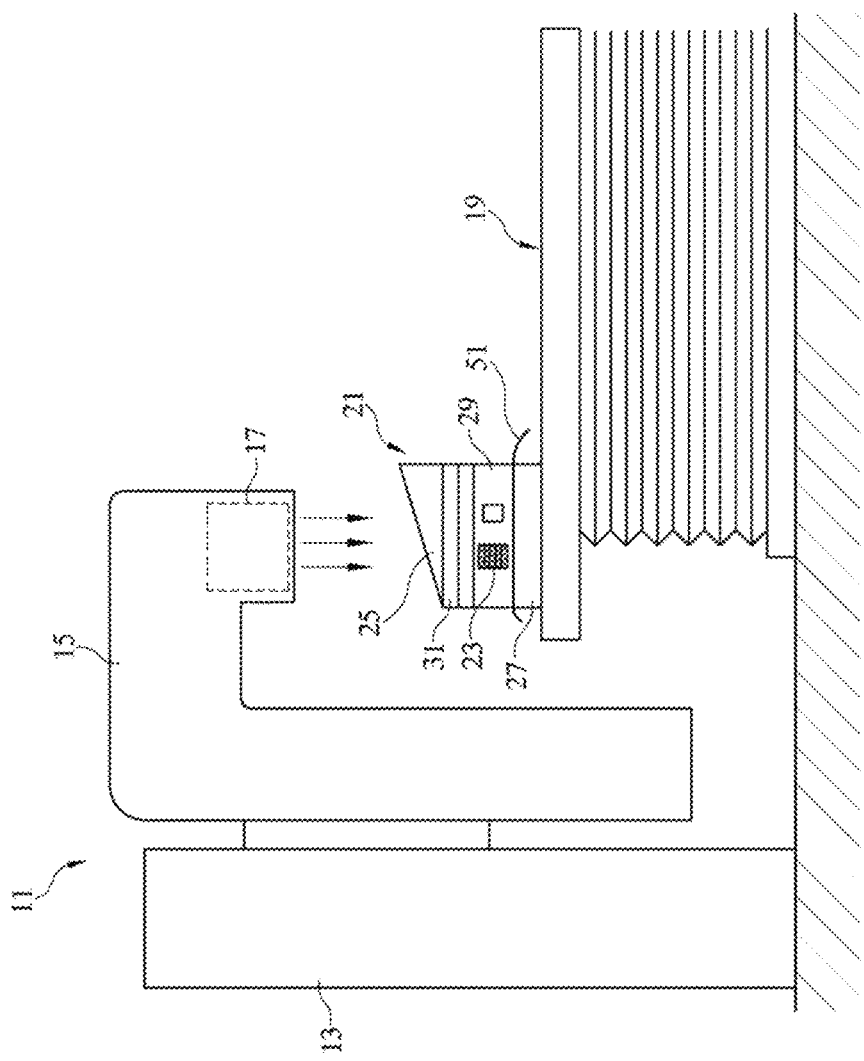
FIG. 1 illustrates an example of a phantom for measuring a radiation dose related with the present invention.
Figure 2:
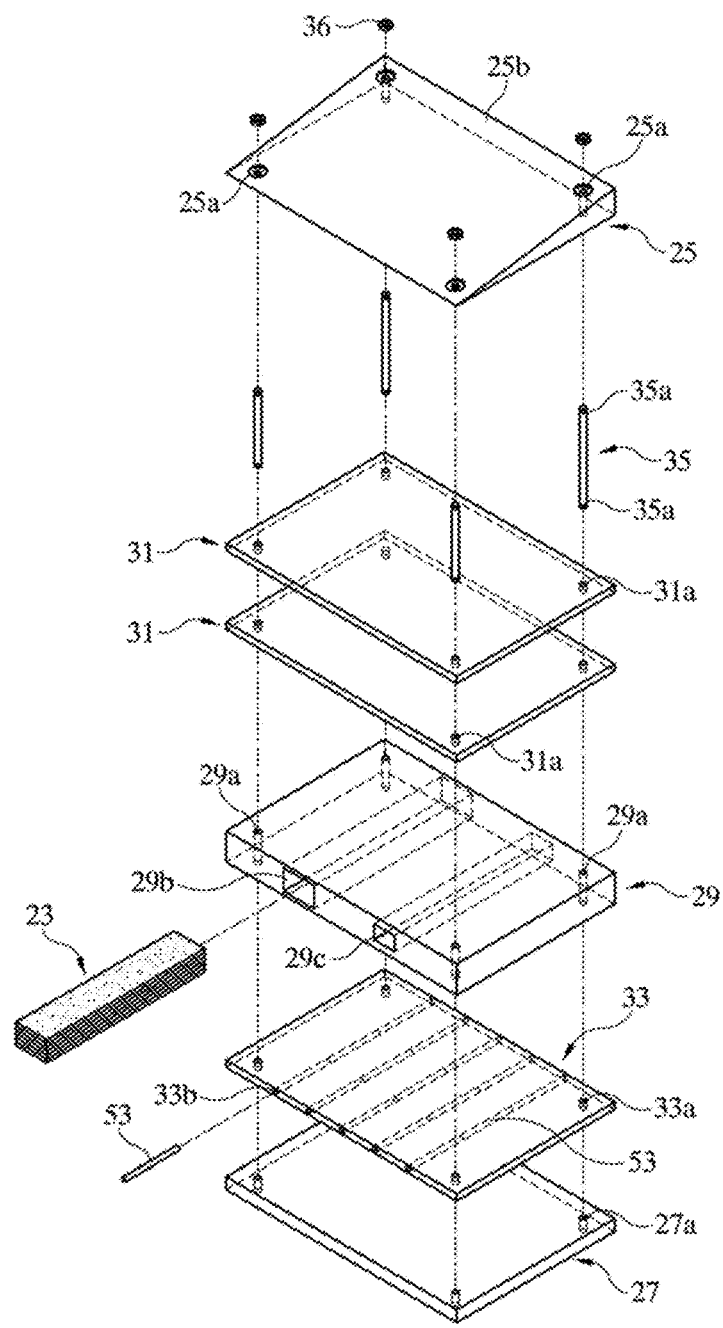
FIG. 2 illustrates an example of an exploded perspective view of the phantom for measuring the radiation dose described in FIG. 1.

FIG. 1 illustrates an example of a phantom for measuring a radiation dose according to the present invention and FIG. 2 illustrates an example of an exploded perspective view of the phantom for measuring the radiation dose described in FIG. 1.

FIG. 1 is a diagram illustrated for describing a used example of a phantom for measuring a radiation dose according to an exemplary embodiment of the present invention and in the exemplary embodiment, a linear accelerator 11 as a radiation emitting apparatus is exemplified.

Referring to FIG. 1, it can be seen that a phantom 21 according to the exemplary embodiment is located at a vertical bottom of a radiation emitting unit 17 while being placed on a treatment table 19. The treatment table 19 is a bed on which a patient to be treated lies by accomplishing a set with the linear accelerator 11.

Further, the linear accelerator 11 is configured by a main body 13, and a rotating gantry 15 rotatably installed on the main body 13.

A high-voltage generator, a microwave generator, or the like is installed in the main body 13, and in the rotating gantry 15, devices such as an acceleration tube accelerating electrons, a magnetic field generator, and the radiation emitting unit 17 are provided. The radiation emitted from the radiation emitting unit 17 is irradiated to tumor of the patient lying on the treatment table 19.

Meanwhile, the phantom 21 according to the exemplary embodiment is set at the vertical bottom of the radiation emitting unit 17 to receive the radiation irradiated downward from the radiation emitting unit 17 and determine a dose of the irradiated radiation.

The phantom 21 is configured by combining at least one base plate 27, a mimetic receiving plate 29 in which various types of mimetics 23 are embedded if necessary, a plurality of flat plates 31, a wedge plate 25, a thermo-luminescence dosimeter mounting plate (hereinafter, referred to as a TLD mounting plate) (33 of FIG. 2), an ion chamber mounting plate (39 of FIG. 3), and the like.

Figure 4:
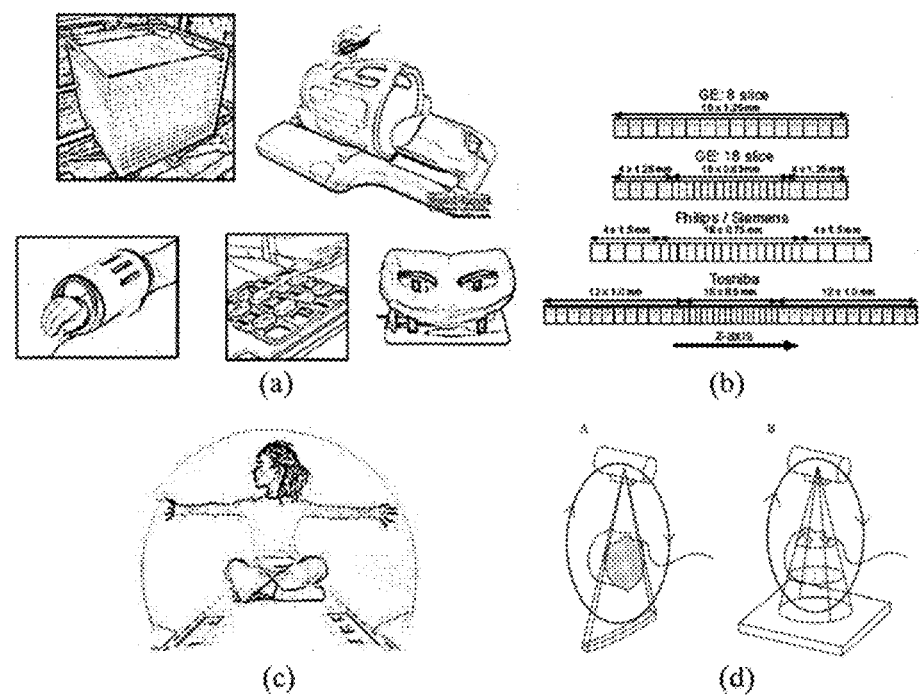
FIG. 4 illustrates a detailed example of different types of medical phantoms related with the present invention.
Figure 5:
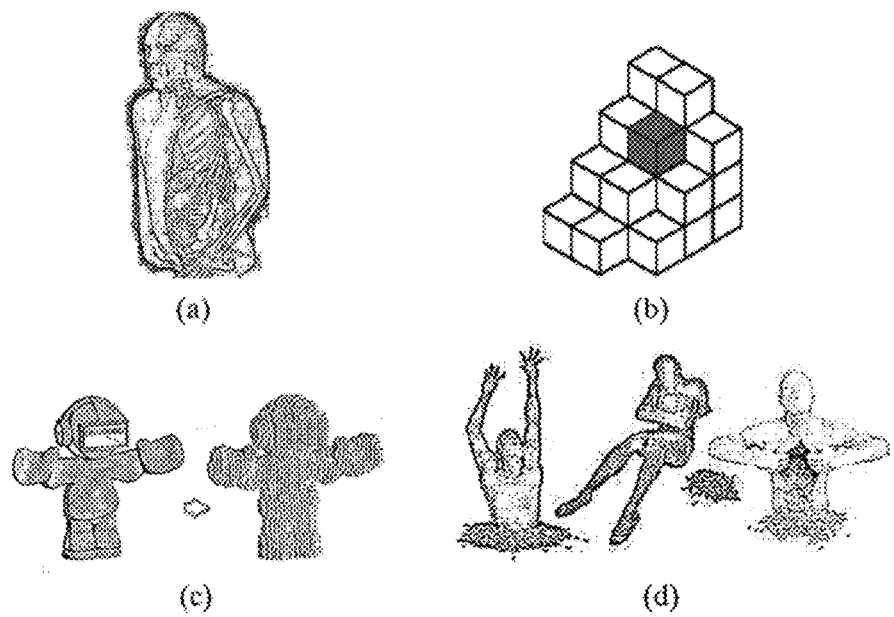
FIG. 5 illustrates a detailed example of modeling the human body in a 3D form related with the present invention.
Figure 6:
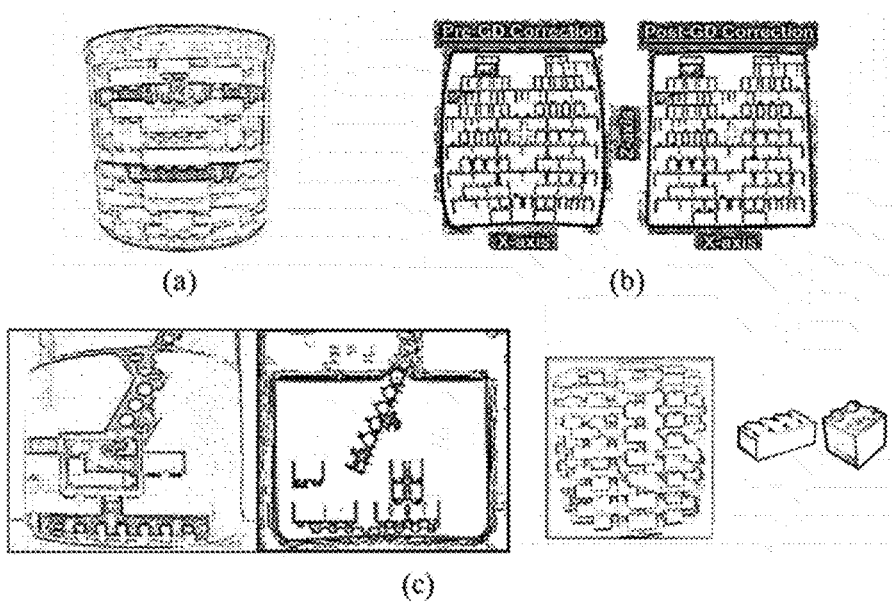
FIG. 6 illustrates a detailed example of modeling the human body by using LEGO blocks.

A combined example of the various constituent elements varies by cases and for example, may have a laminated structure illustrated in FIGS. 4 to 6.

Reference numeral 51 is an X-ray film. The X-ray film 51 is a target of the radiation which sequentially passes through the wedge plate 25, the flat plate 31, and the mimetic receiving plate 29 and an energy level of the radiation reaching the surface thereof is expressed.

As a result, the X-ray film 51 is a radiation dose measuring unit that measures a dose (at the corresponding depth) of the radiation irradiated from the radiation emitting unit 17. In the radiation dose measuring unit, the TLD mounting plate 33 and a thermoluminescent dosimeter (hereinafter, referred to as TLD) (53 of FIG. 2) applied thereto, and the ion chamber mounting plate and an ion chamber applied thereto are further included in addition to the X-ray film 51.

The radiation dose measuring unit has a purpose of measuring a dose of the radiation at a depth where the radiation dose measuring unit is located.

The depth where the radiation dose measuring unit is located varies according to the above-described combined example, and further, which type of mimetic 23 is located or not on the radiation dose measuring unit varies by cases.

FIG. 2 is an exploded perspective view illustrating a combined example of the phantom for measuring the radiation dose according to the exemplary embodiment of the present invention.

As illustrated in FIG. 2, the phantom for measuring the radiation dose according to a combined example has a configuration that includes a base plate 27 having a rectangular plate with a predetermined thickness, a TLD mounting plate 33 laminated on the base plate 27, a mimetic receiving plate 29, a flat plate 31, and a wedge plate 25 that are laminated sequentially on the TLD mounting plate 33, and a fixing rod 35 connecting the constituent elements to each other.

The base plate 27 horizontally supports the TLD mounting plate 33 at a predetermined height from the treatment table 19 while being placed on the treatment table 19 as illustrated in FIG. 1. The base plate 27 adjusts a separation distance between the radiation emitting unit 17 and the radiation dose measuring unit.

For example, the separation distance between the radiation emitting unit 17 and the radiation dose measuring unit may be decreased by increasing a thickness of the base plate 27 or increasing the number of base plates 27.

Female screw holes 27a are formed at four edges of the base plate 27. The female screw hole 27a is a groove having a female thread formed on the inner surface and connected with a male screw portion 35a at the lower end of the fixing rod 35. The fixing rod 35 is extended vertically while being connected to the female screw hole 27a and closely fixes the constituent elements to each other.

The TLD mounting plate 33 is a rectangular acrylic plate having a predetermined thickness and has five TLD receiving holes 33b horizontally extended therein. The TLD receiving holes 33b have a predetermined diameter and are arranged in parallel and both ends thereof are opened to the outside. Of course, the number of TLD receiving holes 33b may vary according to a case.

For reference, acryl has a tissue density corresponding to a density of a general tissue in the body.

A TLD 53 is inserted into the TLD receiving hole 33b. As it is known, the TLD is a dosimeter made of a material having a thermofluorescent property and may be prepared in a chip shape or prepared in a powder shape. The powder shape is sealed in a cylindrical capsule.

In the exemplary embodiment, the capsule-type TLD 53 is used. That is, the capsule-type TLD 53 is inserted to the TLD receiving hole 33b and then pushed up to the central portion to be positioned. Particularly, the plurality of TLDs 53 may be inserted into one TLD receiving hole 33b and also be inserted into only the selected one TLD receiving holes 33b. The TLD 53 receives radiation irradiated from the top while being located in the TLD receiving hole 33b and is removed by an operator later, and a TLD reader (not illustrated) may quantitatively evaluate an exposed radiation dose.

The mimetic receiving plate 29 is provided on the TLD mounting plate 33. The mimetic receiving plate 29 is a hexahedral acrylic block having vertical through holes 29a at four edges and includes two space portions 29b and 29c therein.

The space portions 29b and 29c are horizontally extended in parallel and rectangular holes of which both ends are opened to the outside. Sectional shapes and sizes of the space portions 29b and 29c may vary according to a case.

Basically, the space portions 29b and 29c may be empty according to a mimetic target in the body and may be filled with the mimetic 23. For example, in the case of simulating an empty space such as the oral cavity, the space portion 29c is empty. Further, in the case of simulating the lung, cork which is known to have a similar tissue density to the lung is inserted, and in the case of simulating the bone, Teflon which has a similar tissue density to the bone is inserted. The mimetic 23 may be prepared in a shape of a lump of block, or may be prepared in a thin plate shape and then laminated if necessary. The mimetic receiving plate 29 may not be used in some cases.

The flat plate 31 located on the mimetic receiving plate 29 is a rectangular acrylic plate having various thicknesses.

The flat plate 31 serves to adjust a separation distance of a target from the radiation emitting unit 17. Accordingly, a position of the flat plate 31 or the number of used sheets may vary if necessary. For example, the flat plate 31 may be located between the base plate 27 and the TLD mounting plate 33 and as illustrated in the drawing, also installed between the wedge plate 25 and the mimetic receiving plate 29. Of course, through holes 31a are provided even at four edges of the flat plate 31.

Meanwhile, the wedge plate 25 is an acrylic member having a lateral surface shape of a right triangle. The wedge plate 25 has a horizontal lower surface and a slope 25b inclined at a predetermined angle with the lower surface. A preferable inclined angle of the slope 25b is about 15° to 30°.

Basically, the wedge plate 25 serves to linearly determine a degree of radiation reaching targets with different depths. For example, when the radiation is vertically irradiated to the wedge plate 25 while the x-ray film is located below the wedge plate 25, energy of the radiation is gradually decreased while passing downward through the wedge plate 25 (a thickness of the wedge plate is linearly reduced because the wedge plate is inclined) and the decreased energy of the radiation is reflected to the x-ray film, thereby obtaining information on an attenuation ratio of the radiation to the thickness of the acrylic. When the radiation passes through the thick portion of the wedge plate 25, the attenuation ratio is as high as much and when the radiation passes through a relatively thin portion, the radiation is slightly attenuated.

Even at the four edges of the wedge plate 25, the through holes 25a are formed.

The fixing rod 25 vertically supports the respective constituent elements on the base plate 27 (in this case, a combined example of respective constituent elements may vary), and passes through the through holes 33a, 29a, 31a, and 25a of the TLD mounting plate 33, the mimetic receiving plate 29, the flat plate 31, and the wedge plate 25 and thus, the male screw portion 35 at the lower end thereof is fixed to the female screw hole 27a of the base plate 27.

Reference numeral 36 is a nut which is connected to the male screw portion 25a at the upper end of the fixing rod 35 to fasten and closely contact the constituent elements to each other.

However, in FIGS. 1 and 2, it is assumed that the phantom according to the present invention is to measure the radiation, but the contents of the present invention are not limited thereto and it is apparent that the phantom may be applied for various medical purposes.

Figure 3:
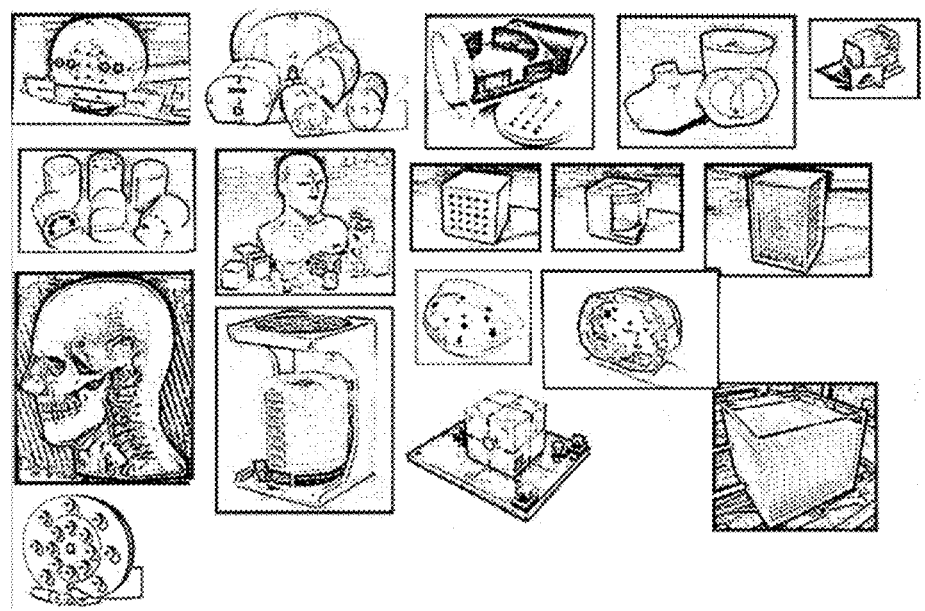
FIG. 3 illustrates various types of medical phantoms related with the present invention.

Meanwhile, FIG. 3 illustrates various types of medical phantoms related with the present invention.

As illustrated in FIG. 3, since a physical mechanism of acquiring an image varies according to an image diagnosis device and a size and a shape of the image diagnosis device are also different, currently, phantoms having various shapes and properties are present.

FIG. 4 illustrates a detailed example of different types of medical phantoms according to the present invention.

That is, as illustrated in FIGS. 4A to 4D, the medical phantoms have no choice but to be prepared in various shapes to be suitable for various sizes and shapes of the image diagnosis device and as a result, the phantoms have no choice but to be limited to characteristics of the device.

Furthermore, in order to create a phantom in a similar shape to the human body, since the phantom needs to be prepared with a similar size to the human body and a medium is added into the phantom, a weight is heavy and there are many difficulties even in an operation.

The human body may be modeled by various methods and particularly, when the human body is simulated, the human body may be modeled by combining voxel units which are small volumes.

In other words, tissues and organs of the human body may be simulated by various combinations of voxels.

FIG. 5 illustrates a detailed example of modeling the human body in a 3D shape according to the present invention.

As shapes illustrated in FIGS. 5A to 5D, the medical phantom may configure a phantom by voxel units by applying the concept and the most implemented phantom is a phantom using LEGO blocks.

Figure 7:
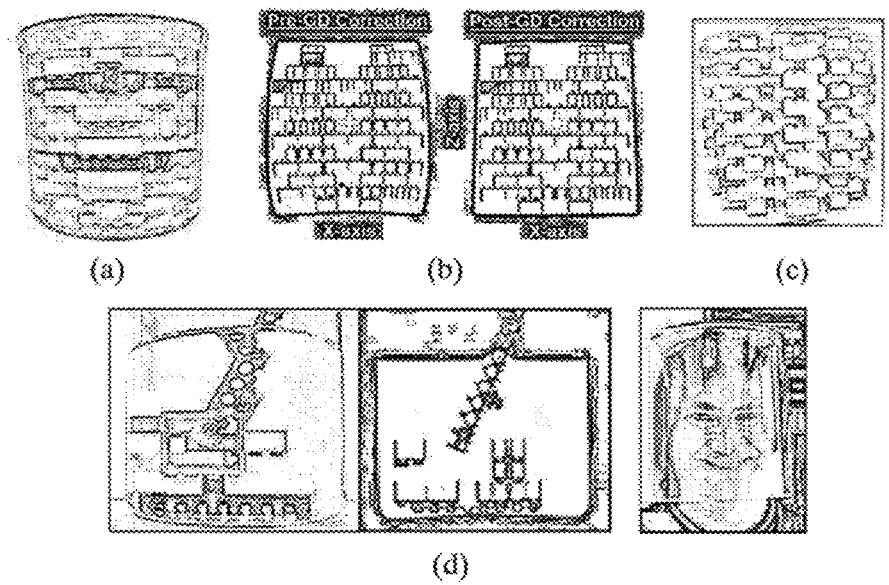
FIG. 7 illustrates another detailed example of modeling the human body by using LEGO blocks.
Figure 8:
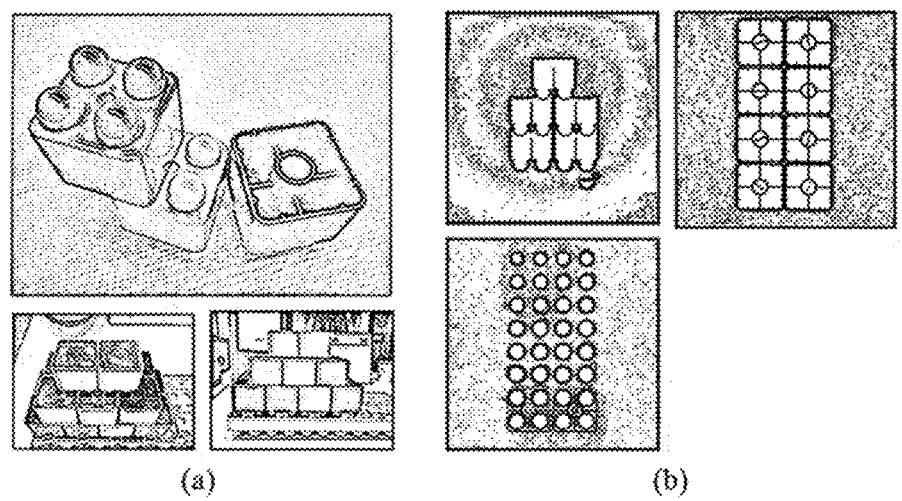
FIG. 8 illustrates a detailed example of an MRI T2 image obtained by filling water in Oxford blocks related with the present invention.

FIG. 6 illustrates a detailed example of modeling the human body by using LEGO blocks, FIG. 7 illustrates another detailed example of modeling the human body by using LEGO blocks, and FIG. 8 illustrates a detailed example of an MRI T2 image obtained by filling water in Oxford blocks according to the present invention.

As illustrated in FIGS. 6A to 8B, in the related art, a phantom is configured in a predetermined shape by combining bricks which are LEGO unit blocks and then may be used in evaluation of performance of the image diagnosis device.

However, in the case of the phantom using the LEGO blocks, since the inside of the blocks is empty, it is disadvantageous that the blocks need to be assembled and then packed in a container with a predetermined size for imaging.

That is, the blocks may be assembled in various shapes, but it is disadvantageous that the blocks have no choice but to be packed in the container in which a signal source for generating a signal source require for imaging is added.

Furthermore, even for evaluating the image and measuring the radiation dose, there is a problem in that a medium having a predetermined physical property is required in the block.

As a result, in the case of the phantom using the LEGO blocks, the degree of freedom of the blocks is limited depending on a size and a shape of the container and the phantom has the same problem as a phantom which is widely used in the related art.

Further, the most important disadvantage of the LEGO blocks is not prepared for the medical phantom and thus, there are many limitations to use the size, the shape, and the function for a medical use.

Further, since the LEGO shape has ridges and furrows in the blocks, when the LEGO shape is simply imaged by combining the blocks, the LEGO shape has a complicated shape and thus, it is very disadvantageous for medical use of the image.

Particularly, in the case of combining LEGO blocks having small physical sizes, the complexity is very increased and when the physical size is relatively large, it is disadvantageous in a detailed simulation of the characteristics of the human body.

Therefore, the present invention provides unit blocks for multiple purposes and multiple images, a multi-module medical phantom using unit blocks, and a control method thereof. Particularly, the present invention provides unit blocks configuring a phantom, a method for preparing unit blocks which may fill a medium required for imaging therein and have a shape and a structure in which image quality evaluation, dosimetry, and interventional operation training are possible.

That is, the unit block proposed in the present invention may be prepared in a hexahedral shape to fill the medium therein.

A basic shape of the unit block according to the present invention is configured by only a hexahedron and an application shape may have a structure in which the blocks are tightly coupled with each other with ridges (males) at the top of the block and furrows (females) at the bottom of the block.

The unit blocks having the basic shape and the application shape provided according to the present invention may be configured with various shapes and sizes in various combinations.

In this case, in the inside of the unit block, $CuSO_4$, $MnCl_2$, and $NiCl_2$ which are signal sources required for magnetic resonance imaging and Gd-based media, iron oxide-based media, and gel-type media which are capable of exhibiting a contrast effect may be filled.

Further, in the inside of the unit block, a medium such as water, iodine, barium, $CaCO_3$, paraffin, and adipose that may perform image evaluation in X-ray computer tomography may be filled and positron-emitting isotopes and gamma-emitting isotopes may be filled as signal source of a PET and a SPECT which are nuclear medical imaging devices.

Particularly, not only imaging in a single imaging device but also multiple imaging in multiple imaging devices are enabled by various combinations of unit blocks.

Further, the block-based phantom configured above may be used for dose evaluation of radiation treatment and temperature measurement of heat treatment.

Further, an image quality evaluation module is added the inside of the unit blocks to evaluate spatial resolution, contrast resolution, signal-to-noise ratio, uniformity, location and accuracy of cross-section selection, geometric accuracy, and the like through combination of unit blocks.

Particularly, the image quality evaluation module is used with the phantom used for the image quality evaluation in the related art to support quality information on a photographing area which is not imaged by the existing phantom to be acquired.

Figure 9:
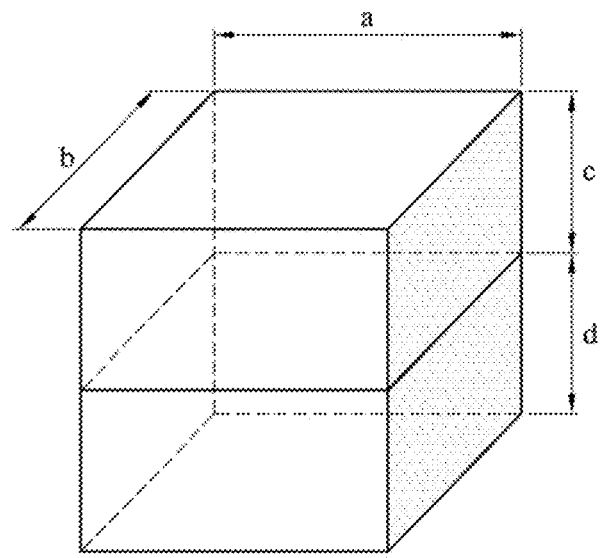
FIG. 9 illustrates a basic form of a unit block proposed in the present invention.

FIG. 9 illustrates a basic shape of a unit block proposed in the present invention.

FIG. 9 illustrates a configuration of a unit block having a basic shape according to the present invention, and in FIG. 9, a means a block (phantom) length, b means a block (phantom) width, c means a block (phantom) height, and d means a block (cap) height.

The inside of the unit block according to the present invention illustrated in FIG. 9 is an empty space and has a structure which may be sealed by adding the medium suitable for medical imaging therein.

A lateral surface of the unit block according to the present invention has two holes, and a medium may be injected through one hole and the injected medium and internal air may be discharged through another hole so as to prevent the air from being generated therein.

Figure 10:
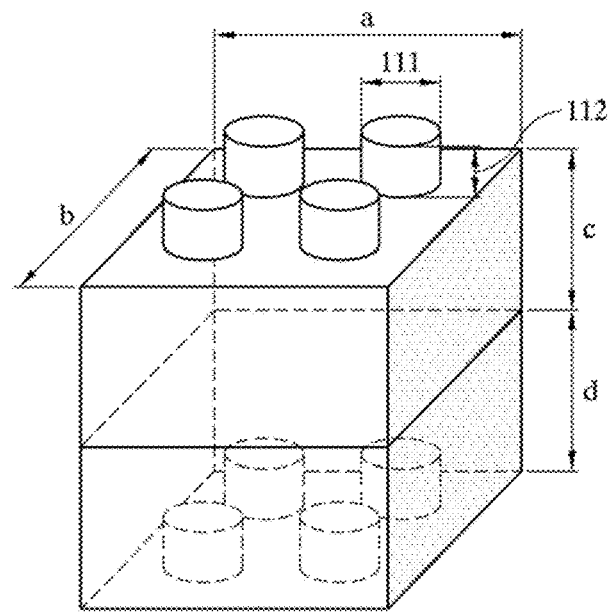
FIGS. 10 to 12 illustrate examples of application shapes of the unit block proposed in the present invention.
Figure 11:
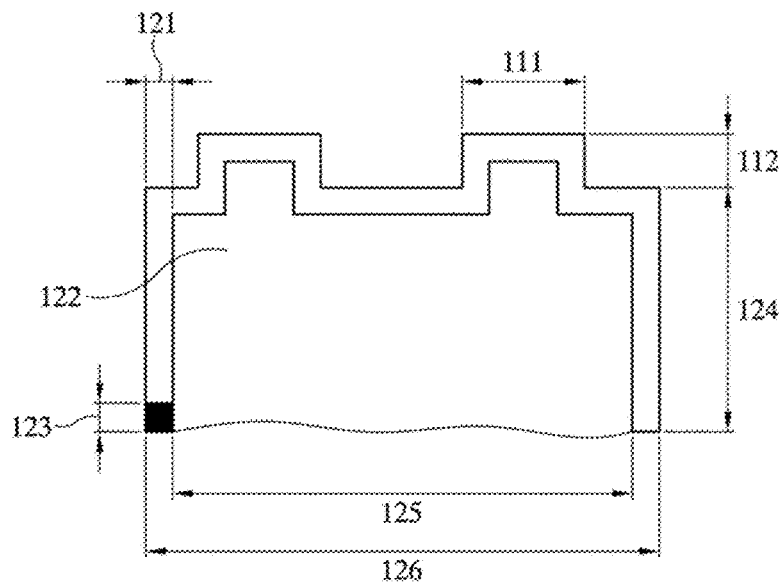
Figure 12:
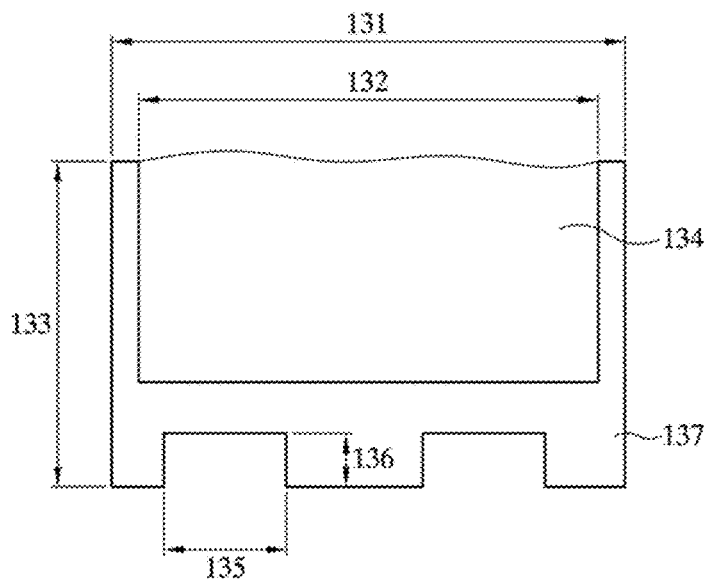

Meanwhile, FIGS. 10 to 12 illustrate examples of application shapes of the unit block proposed in the present invention.

In FIGS. 10 to 12, the contents of the configuration of the unit block having the application shape are illustrated.

In FIGS. 10 to 12, 111 means a height of a socket, 112 means a width of the socket, 121 means a thickness of a container, 122 means a fluid of the phantom, 123 means an inlet of the phantom fluid, 124 means a height of the block (phantom), 125 means a width of the block (phantom) inlet, and 126 means a width of an outlet of the block (phantom).

Further, 131 means a width of an outlet of a block (cap), 132 means a width of an inlet of the block (cap), 133 means a height of the block (cap), 134 means a phantom fluid, 135 means a container material, 136 means a width of the socket, and 137 means a height of the socket.

Referring to FIGS. 10 to 12, the unit block having an application shape is configured by ridges and furrows, and the unit blocks can be assembled and disassembled to and from each other and are configured by various combinations.

The ridge portion has a cube shape and the furrow may be exactly attached to the cube of the ridge portion.

Further, the inside of the unit block is an empty space and configured by a structure which may be sealed by adding the medium suitable for the purpose therein.

Further, a lateral surface except for the ridges and the furrows of the unit block has two holes, and a medium may be injected through one hole and the injected medium and internal air may be discharged through another hole so as to prevent the air from being generated therein.

That is, the unit block according to the present invention is a unit block configured by only a hexahedron and an application type block with ridges (males) at the top of the block and furrows (females) at the bottom of the block, and may be a structure which can combine a basic unit block and an application type block.

Therefore, the unit blocks having the basic shape and the application shape provided according to the present invention may be configured with various shapes and sizes in various combinations.

In this case, in the inside of the unit block, $CuSO_4$, $MnCl_2$, and $NiCl_2$ which are signal sources required for magnetic resonance imaging and Gd-based media, iron oxide-based media, and gel-type media which are capable of exhibiting a contrast effect may be filled.

Further, in the inside of the unit block, a medium such as water, iodine, barium, CaCO3, paraffin, and adipose that may perform image evaluation in X-ray computer tomography may be filled and positron-emitting isotopes and gamma-emitting isotopes may be filled as signal source of a PET and a SPECT which are nuclear medical imaging devices.

Particularly, not only imaging in a single imaging device but also multiple imaging in multiple imaging devices is enabled by various combinations of unit blocks.

Figure 13:
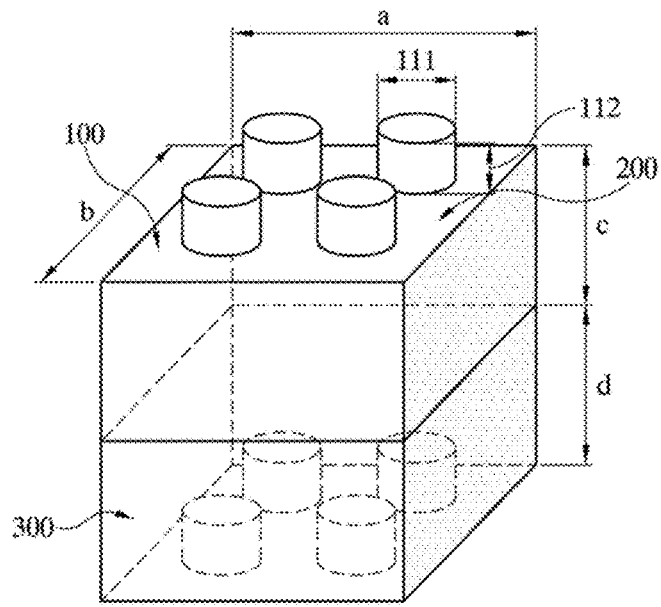
FIG. 13 illustrates a form of a stem block phantom proposed by the present invention.

Meanwhile, FIG. 13 illustrates a shape of a stem block phantom proposed by the present invention.

FIG. 13 illustrates the content in which in the inside of the unit block, $CuSO_4$, $MnCl_2$, and $NiCl_2$ which are signal sources required for magnetic resonance imaging and Gd-based media, iron oxide-based media, and gel-type media which are capable of exhibiting a contrast effect may be filled.

Referring to FIG. 13, in the inside of the unit block, a medium such as water, iodine, barium, $CaCO_3$, paraffin, and adipose that may perform image evaluation in X-ray computer tomography may be filled and positron-emitting isotopes and gamma-emitting isotopes may be filled as signal source of a PET and a SPECT which are nuclear medical imaging devices.

Figure 14:
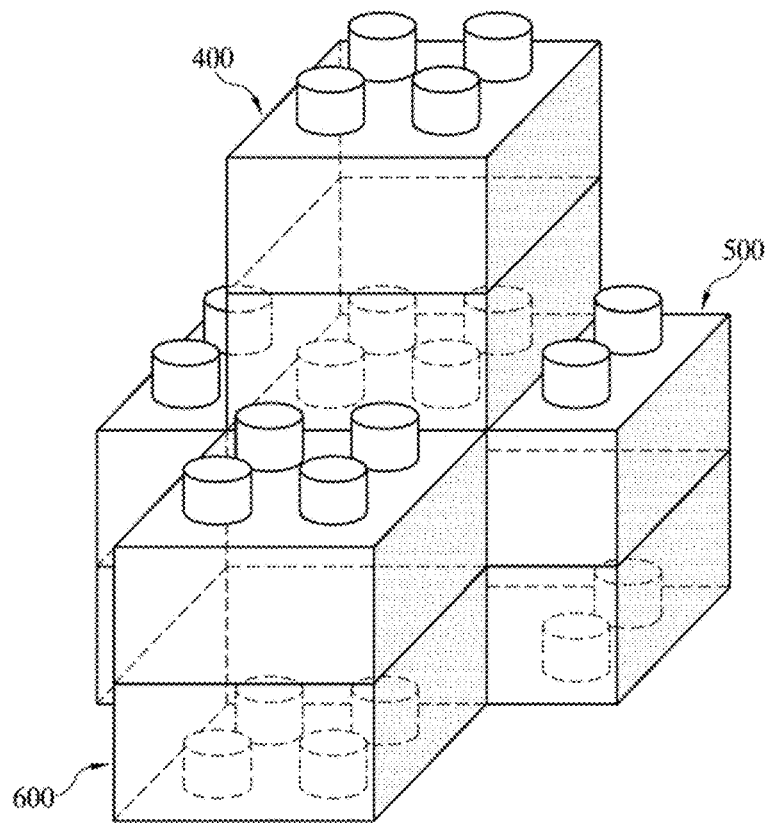
FIG. 14 illustrates a detailed form of a stem block phantom applied to multipurpose multiple imaging according to the present invention.

Further, FIG. 14 illustrates a detailed shape of a stem block phantom applied to multiple purposes and multiple images according to the present invention.

That is, FIG. 14 illustrates a basic diagram in which not only imaging in a single imaging device but also multiple imaging in a multiple imaging device are enabled through various combinations of the unit blocks.

The block-based phantom configured in FIG. 14 may be used even in evaluation of a dose of the radiation treatment and a temperature measurement of heat treatment as well as the multiple imaging devices.

Figure 15:
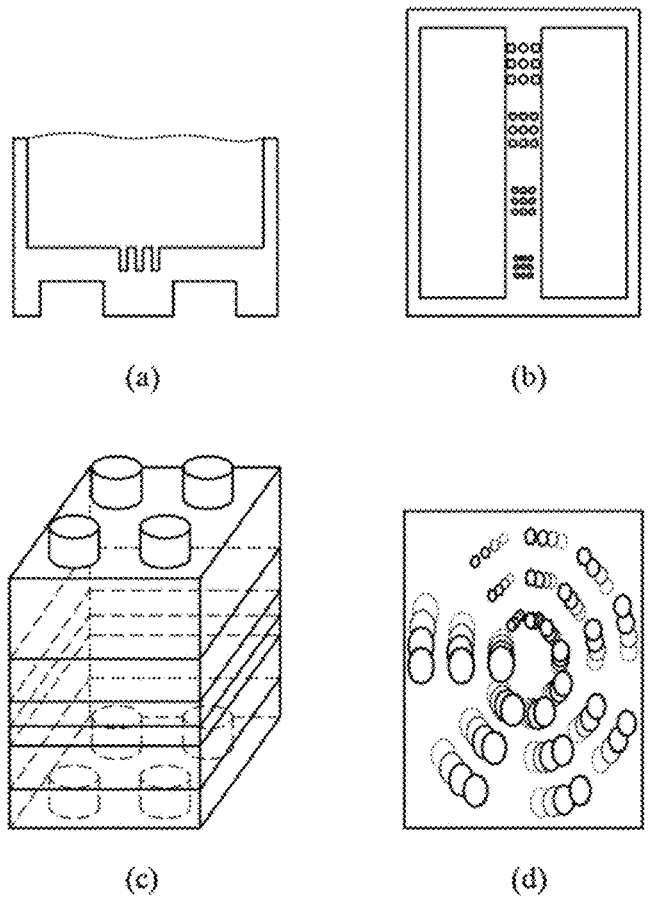
FIGS. 15 to 17 illustrate a detailed form of a QA/AC Module to which the stem block phantom applied to multipurpose multiple imaging is applied according to the present invention.
Figure 16:
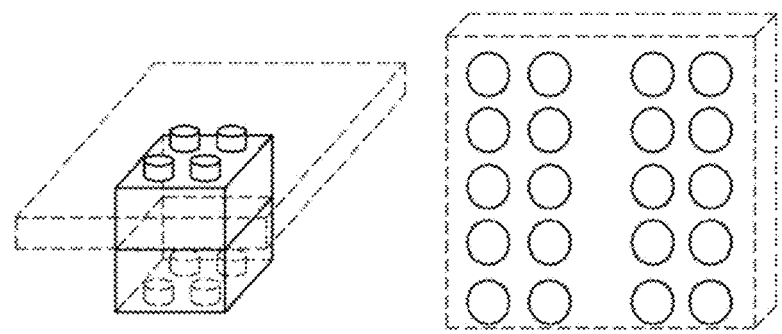
Figure 17:
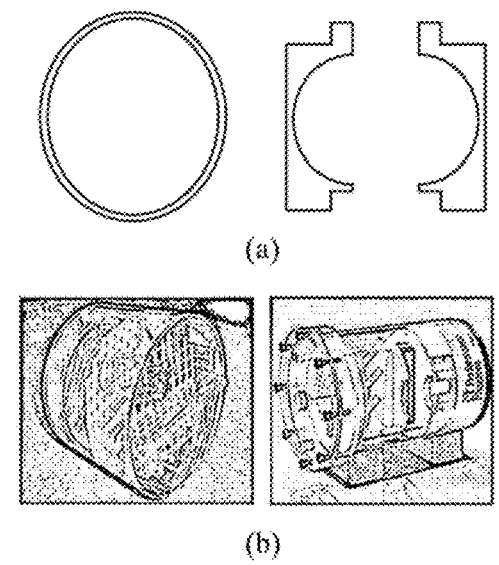

Meanwhile, FIGS. 15 to 17 illustrate a detailed shape of a QA/AC Module to which the stem block phantom applied to multiple purposes and multiple images is applied according to the present invention.

That is, FIGS. 15 to 17 illustrate module diagrams in which an image quality evaluation module is added the inside of the unit blocks to evaluate spatial resolution, contrast resolution, signal-to-noise ratio, uniformity, location and accuracy of cross-section selection, and geometric accuracy, and the like through combination of unit blocks.

Referring to FIGS. 15 to 17, the image quality evaluation module is used with the phantom used for the image quality evaluation in the related art to acquire quality information on a photographing area which is not imaged by the existing phantom.

Meanwhile, the present invention may additionally provide a shape and a configuration of a human body module mapping phantom suitable for multiple purposes and multiple fusion medical images.

The module mapping phantom proposed in the present invention may be configured by a set of unit blocks, a special purpose module, and an accessory.

Herein, the unit block set may be configured by unit blocks which are half units, double units, and square units which are half, double, and square in horizontal and vertical sizes based on a hexahedral unit.

Further, the unit block set may be configured by unit blocks which are double disks, quarter disks, and quarter double disks which are double, quarter, and quarter double in the horizontal and vertical sizes based on a disk.

Further, there is an advantage that the unit blocks may be configured by another shape like wooden blocks for baby toys.

Further, respective unit blocks may be tightly coupled with each other by using a stud-and-tube coupling method which is a LEGO coupling system.

Particularly, the blocks may be easily separated from each other to prevent deformation of the unit block by strong external force.

Meanwhile, the unit blocks have at least one solution injection port, and the solution may be injected into the unit block through the solution injection port and the filled solution may be removed.

Further, the unit blocks may be prepared by using polycarbonate which is a semi-transparent material.

In the case of the unit blocks prepared by using polycarbonate, since the internal material may be visually confirmed from the outside, the presence of air bubbles can be easily visualized when the solution is injected.

Particularly, in the case of injecting a dyed solution, the injection solution may be easily distinguished between unit blocks and leakage of radiation medicals used in nuclear medical imaging may be easily confirmed.

Further, a physical evaluation structure used for the medical image quality evaluation may be configured to be inserted into the unit blocks by module mapping.

The evaluation structure may be prepared according to a standard proposed in American College of Radiology (ACR), American Association of Physicists in Medicine (AAPM), and National Electrical Manufacturers Association (NEMA) and the structure may be inserted into the unit blocks to be equally used with the unit blocks.

As a result, the spatial resolution of the medical image, the contrast discrimination power, the linearity of the CT number, the section selection accuracy and the section position accuracy, the signal-to-noise ratio, the image uniformity, the geometric distortion degree, and the like may be evaluated.

Particularly, a rotate connector that enables diagonal coupling of the unit blocks other than linear coupling, a jig and a fixed frame that strongly support the coupling between the unit block and the module, and an external module that can induce additional attenuation in projection and emission tomographic images are prepared to variously evaluate performance of the image system in addition to the existing medical image quality evaluation.

Figure 18:
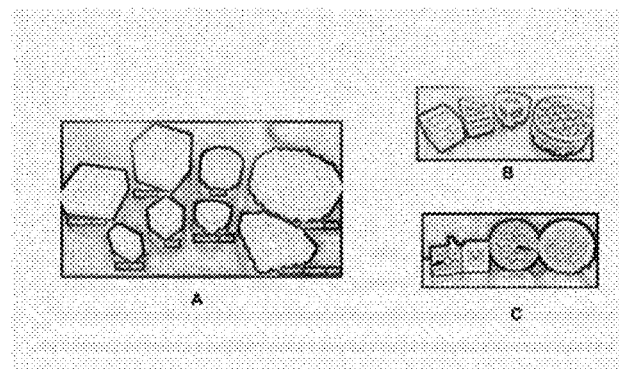
FIG. 18 illustrates a detailed example of unit blocks of the module mapping phantom related with the present invention.

FIG. 18 illustrates a detailed example of unit blocks of the module mapping phantom related with the present invention.

Referring to FIG. 18, in FIG. 18A, unit blocks may be configured in 8 basic shapes and various types of phantoms may be assembled by combination of the basic unit blocks.

Further, in FIG. 18B, unit blocks are hollow and semi-transparent to be easily distinguished from the outside when the dyed solution is injected therein.

Further, the solution is easily injected and removed through a bolt-nut type injection port.

In FIG. 18C, unit blocks have a stud-and-tube coupling system and thus, the blocks are easily coupled to and separated from each other.

Figure 19:
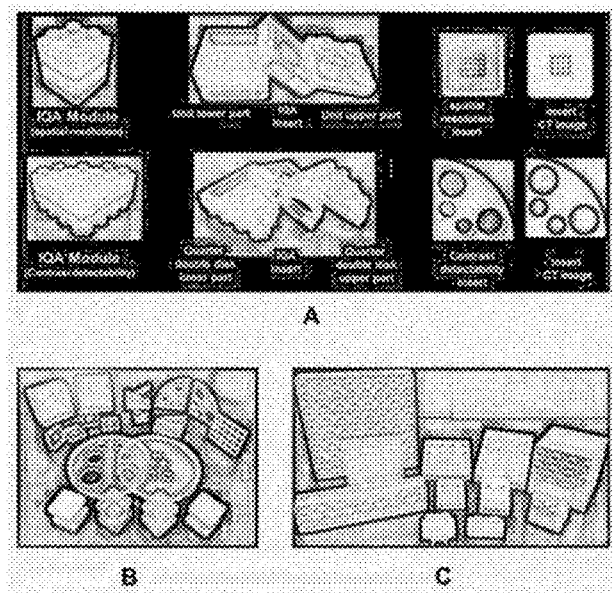
FIG. 19 illustrates a detailed example of a configuration of a medical image quality evaluation module related with the present invention.

FIG. 19 illustrates a detailed example of a configuration of a medical image quality evaluation module related with the present invention.

Referring to FIG. 19, the medical image quality evaluation module illustrated in FIG. 19A is configured by inserting and laminating the image evaluation structure in the unit block.

Photographs are a representative structure for detecting spatial resolution and contrast and CT images.

FIG. 19B is a structure for evaluating spatial resolution, contrast discrimination power, linearity of CT numbers, section selection accuracy and section position accuracy, signal-to-noise ratio, image uniformity and geometric distortion, which is inserted into the image quality module.

FIG. 19C illustrates a rotate connector, a jig, and a fixture which increase coupling diversity between blocks or modules.

Figure 20:
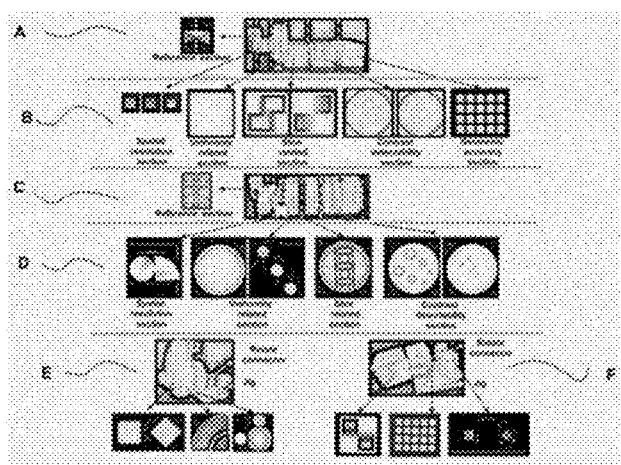
FIG. 20 illustrates a detailed example of the image evaluation module related with the present invention.

FIG. 20 illustrates a detailed example of the image evaluation module related with the present invention.

Referring to FIG. 20, FIG. 20A illustrates a combination of image evaluation modules for MRI image quality evaluation and FIG. 20B illustrates an MRI image corresponding to each item of the image quality proposed in the ACR.

Further, FIG. 20C illustrates a combination of unit blocks for CT image quality evaluation in AAPM, FIG. 20D illustrates an CT image corresponding to each item of the image quality, and FIGS. 20E and 20F illustrate a combination of image evaluation modules used for a partial volume effect, radiation quality hardening, and performance evaluation of an inclined cross-section by using the rotate connector and the jig in the MRI and the CT and CT and MRI images.

Figure 21:
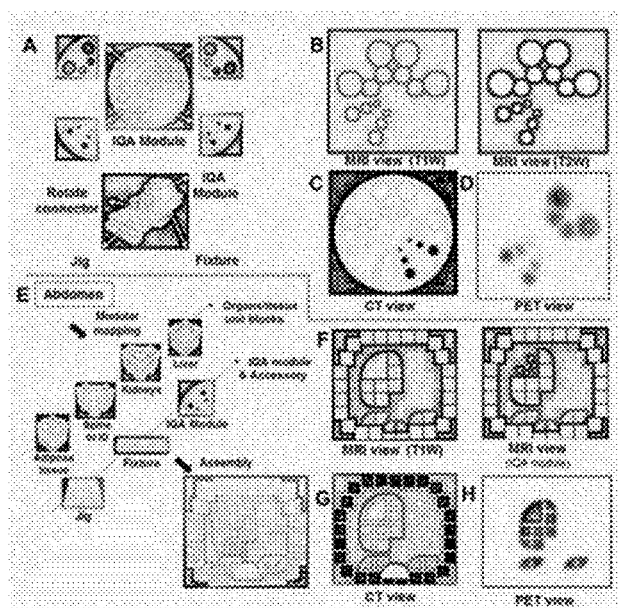
FIG. 21 illustrates another detailed example of the image evaluation module related with the present invention.

FIG. 21 illustrates another detailed example of the image evaluation module related with the present invention.

Referring to FIG. 21, FIG. 21A illustrates an image evaluation module for evaluating feasibility of multiple image application and a combination of a rotate connector, a jig, and a fixture, and each image modality has unique image contract and may be confirmed through the image evaluation module.

Further, FIG. 21B illustrates an MRI image acquired by T1 and T2 weighted images of a contrast detection image evaluation module, FIG. 21C illustrates a CT image of the contrast detection image evaluation module, and FIG. 21D illustrates a detailed example of a PET image of the contrast detection image evaluation module.

Further, FIG. 21E illustrates unit blocks of liver, kidney, spine, and adipose tissue by module mapping of the human abdomen and an image evaluation module, and the human body may be decomposed into organs and tissues to be configured as a module mapping phantom.

Further, FIG. 21F illustrates a T1 weighted image of the combined module mapping phantom and a T1 weighted image to which the image evaluation module is inserted, FIG. 21G illustrates a CT image of the combined module mapping phantom, and FIG. 21H illustrates a PET image of the combined module mapping phantom.

When the embodiment of the present invention is applied, the module mapping phantom may be used to be suitable for a single, multiple, and fusion medical devices according to a combination of unit blocks, modules, and accessories unlike an integrated built-in phantom in the related art.

In particular, since the module mapping phantom having consistency and standardization which are advantages of a module system is suitable as a basic phantom of medical image quantification, it will be very important to construct reliable medical image big data through the medical image quantification in the future.

Meanwhile, the consistency and standardization of a measurement result through the phantom for performance evaluation, quality control, and dosimetry of a medical imaging device are very important factors in the single and fusion medical device.

In particular, unlike the integrated built-in phantom in the related art, since the module type phantom has advantages of efficiency, feasibility, and diversity in the R & D, production, procurement and marketing, low cost and high efficiency by integrating production lines, and rapid response to a market change, it is expected that the module type phantom will be widely spread and used in a medical device industry, a research institute and a clinical institution.

Further, when the configuration of the present invention is applied, the block based phantom may be combined in various forms according to the combination of the blocks and used for multiple images and multiple purposes unlike a phantom having a single image and a single purpose, which is heavy and difficult to operate.

In particular, since the unit block is very easy to mass-produce and may be used in various imaging devices, the unit block is very economical.

In addition, performance evaluation, quality control, and dosimetry of imaging devices are very important factors in a medical field and since the factors may be used in all clinical institutions due to the characteristics of blocks that may be combined in various forms, the factors are widely spread and used, thereby providing a business value and marketability to the user.

Meanwhile, the present invention may be implemented as a computer readable code in a computer readable recording medium. The computer readable recording medium includes all kinds of recording devices storing data which may be deciphered by a computer system. Examples of the computer readable recording medium include a ROM, a RAM, a CD-ROM, a magnetic tape, a floppy disk, an optical data storage device, and the like and further include a device implemented as a type of a carrier wave (for example, transmission through the Internet). Further, the computer readable recording media may be stored and executed as codes which may be distributed in the computer system connected through a network and read by a computer in a distribution method. In addition, functional programs, codes, and code segments for implementing the present invention may be easily inferred by programmers in the related art.

Further, in the aforementioned apparatus and method, configurations and methods of the described embodiments may not be limitatively applied but all or some of the respective embodiments may be selectively combined and configured so as to be variously modified.

The invention claimed is:

1. A medical phantom which models at least a part of a human body by using a plurality of unit blocks,
wherein the plurality of unit blocks include: a first unit block having a hexahedral shape of which the inside is empty; and a second unit block having a shape, of which the inside is empty, different from the hexahedral shape, having a plurality of ridges formed at the upper end thereof for stud-and-tube coupling, and having a plurality of furrows formed at the lower end thereof and enabled to be coupled to the plurality of ridges, wherein the medical phantom is determined according to a combination form of the first unit block and the second unit block, at least one hole is formed on the lateral surfaces of the first unit block and the second unit block and a medium is injected through the at least one hole; and wherein the media injected through the first hole includes $CuSO_4$, $MnCl_2$, and $NiCl_2$ which are signal sources required for magnetic resonance imaging and Gd-based media, iron oxide-based media, and gel-type media which are capable of exhibiting a contrast effect.

2. The medical phantom of claim 1, wherein the second unit block includes a 2-1st block which is a half in a vertical size larger than the first unit block, a 2-2nd block which is twice in vertical size larger than the first unit block, and a 2-3rd block which is a square of the vertical size of the first unit block.

3. The medical phantom of claim 1, wherein the second unit block includes, based on a predetermined disk shape, a 2-4th block which is twice in horizontal and vertical sizes larger than the disk shape, a 2-5th block which is ¼ in horizontal and vertical sizes larger than the disk shape, and a 2-6th block which is twice in horizontal and vertical sizes larger than the disk shape.

4. The medical phantom of claim 1, wherein the plurality of ridges is in a cylindrical shape which protrudes at the upper end of the second unit block and the plurality of furrows is formed at the lower end of the second unit block in a recessed cylindrical shape to be coupled with the plurality of ridges.

5. The medical phantom of claim 1, wherein the first unit block and the second unit block are made of polycarbonate which is a semi-transparent material.

6. The medical phantom of claim 5, wherein a plurality of media injected through the at least one hole have different colors and the media injected through the at least one hole are enabled to be distinguished by using a semi-transparent property of the polycarbonate and a characteristic in which the colors of the media are different from each other.

7. The medical phantom of claim 1, wherein the media injected through the first hole include water, iodine, barium, $CaCO_3$, paraffin, and adipose capable of image evaluation in X-ray computed tomography.

8. The medical phantom of claim 1, wherein the media injected through the first hole include positron-emitting isotopes and gamma-emitting isotopes which are the signal sources of PET and SPECT which are nuclear medical imaging devices.

9. The medical phantom of claim 1, wherein at least some of the media and air in the first and second unit blocks are output to the outside through the at least one hole.

10. The medical phantom of claim 1, wherein the medical phantom determined according to a coupling shape of the first and second unit blocks is enabled to be used for multiple purposes and is connected with multiple imaging devices to support multiple imaging.

11. The medical phantom of claim 1, further comprising:
image quality evaluation modules provided in the first and second unit blocks,
wherein the medical phantom is capable of evaluating at least some of spatial resolution, contrast resolution, signal-to-noise ratio, uniformity, location and accuracy of cross-section selection, and geometric accuracy using the image quality evaluation module.

12. An image diagnostic apparatus using the medical phantom of claim 1.

* * * * *